(12) United States Patent
Del Barrio et al.

(10) Patent No.: US 8,309,105 B2
(45) Date of Patent: Nov. 13, 2012

(54) TRIFLUSAL-CONTAINING POLYMERS FOR STENT COATING

(75) Inventors: Julio San-Román Del Barrio, Madrid (ES); Gema Rodríguez Crespo, Madrid (ES); Mar Fernández Gutiérrez, Madrid (ES); Alberto Gallardo Ruiz, Madrid (ES); Luis Duocastella Codina, Barcelona (ES); Maria Molina Crisol, Barcelona (ES)

(73) Assignee: Palau Pharma, S.A., Palau-Solia i Plegamans (ES)

( * ) Notice: Subject to any disclaimer, the term of this patent is extended or adjusted under 35 U.S.C. 154(b) by 1093 days.

(21) Appl. No.: 12/067,563

(22) PCT Filed: Sep. 20, 2006

(86) PCT No.: PCT/EP2006/009156
§ 371 (c)(1),
(2), (4) Date: Apr. 23, 2008

(87) PCT Pub. No.: WO2007/014787
PCT Pub. Date: Feb. 8, 2007

(65) Prior Publication Data
US 2008/0249617 A1    Oct. 9, 2008

(30) Foreign Application Priority Data
Sep. 21, 2005   (EP) .................................... 05380204

(51) Int. Cl.
*A61F 2/82* (2006.01)
*A61L 27/34* (2006.01)
*C08G 63/02* (2006.01)

(52) U.S. Cl. ....... 424/400; 623/1.42; 623/1.46; 424/423
(58) Field of Classification Search .................. 424/400; 623/1.42, 1.46
See application file for complete search history.

(56) References Cited

U.S. PATENT DOCUMENTS
6,979,465 B1    12/2005   Gallardo Ruiz et al.

FOREIGN PATENT DOCUMENTS
EP    120954    * 6/2002

OTHER PUBLICATIONS

Troelstra, E.J., Chemical Engineering Science, vol. 51, No. 10, pp. 2479-2488, 1996.*
Troelstra et al. (Chemical Engineering Science, vol. 51, No. 10, pp. 2479-2488, 1996).*
Bauerova, K., et al., "Study of in vitro kinetics and liberation mechanism of pentoxifylline from coated pellets and compacts based on 2-hydroxyethylmethacrylate-butyl acrylate copolymer," Drug Development and Industrial Pharmacy, 14(15-17): 2477-97 (1988).
Gallardo, Alberto, "A Kinetic Model to Explain the Zero-Order Release of Drugs from Ionic Polymeric Drug Conjugates: Application to AMPS-Triflusal-Derived Polymeric Drugs," Macromolecules, 36(23): 8876-8880 (Nov. 18, 2003).
Rodriguez, Gema, et al., "Hydrophilic Polymer Drug from a Derivative of Salicylic Acid: Synthesis, Controlled Release Studies and Biological Behavior," Macromol. Biosci., 4(6): 579-586 (Jun. 25, 2004).
Rodriguez, G., et al., "New resorable poymeric systems with antithrombogenic activity," Journal of Materials Science: Materials in Medicine, 10: 873-878 (1999).
Tanabe, Kengo, et al., "Local Drug Delivery Using Coated Stents: New Developments and Future Perspectives," Current Pharmaceutical Design, 10(4): 357-367 (2004).
International Preliminary Report on Patentability and Written Opinion of the International Searching Authority for PCT/EP2006/009156, dated Mar. 26, 2008.

* cited by examiner

*Primary Examiner* — Fereydoun G Sajjadi
*Assistant Examiner* — Anna Falkowitz
(74) *Attorney, Agent, or Firm* — Rothwell, Figg, Ernst & Manbeck PC

(57) ABSTRACT

New triflusal-containing polymeric compounds resulting from the polymerization of 2-(methacryloyloxy)ethyl 2-acetyloxy-4-(trifluoromethyl)benzoate with butyl acrylate are described. These new polymers exhibit good adhesion and crack-bridging properties and are particularly suitable for the coating of stents.

13 Claims, 3 Drawing Sheets

TRIFLUSAL-CONTAINING POLYMERS FOR STENT COATING

This application is a 371 filing of PCT/EP2006/009156, filed Sep. 20, 2006, which claims priority from European application number 05380204.7, filed Sep. 21, 2005. These prior applications are incorporated herein by reference.

The present invention relates to a new series of triflusal-containing polymers, which are particularly useful as a coating for stents. The invention also relates to a process for the preparation of these polymers, as well as to their use as a stent coating.

BACKGROUND OF THE INVENTION

Percutaneous coronary interventions such as angioplasty are a safe, effective way to open blocked coronary arteries. Initially, angioplasties were performed only with a balloon. An important advance of this technique was the development of stents, which are small expandable, usually metallic, tubular structures that are introduced up to the site of the obstruction and used to keep the artery open.

Despite the huge advance made with this technique (more than one million surgeries of this kind are performed per year worldwide), the long-term results are still not satisfactory due to the onset of restenosis. Restenosis is the vessel reocclusion that occurs, generally at 6 months, after an initially successful percutaneous coronary intervention. Unlike atherosclerotic lesions, restenosis is a lesion healing process in response to damage to the artery wall induced during the placement of the stent.

In order to try to overcome the problem of restenosis, development has begun on stents that incorporate drugs, what is known as Drug Eluting Stents (DES). Although the drug can be incorporated into the stent directly in reservoirs constructed in the stent, the DES generally consist of stents coated with polymers into which the drug has been incorporated, either by chemically bonding the drug to the polymer or more usually by embedding the drug inside the polymer.

The polymer to be used in DES must meet a number of extremely stringent requirements. Among others, it must be stable, biocompatible, and neither thrombogenic nor proinflammatory. It also must allow loading with sufficient amounts of the anti-restenosis drug to obtain the desired dosing levels and must be capable of releasing the drug in a controlled manner over a period of various weeks. In particular, however, the polymer must exhibit elevated adhesion to the metal surface of the stent as well as high flexibility and absence of crack-bridging, since it is necessary that the polymer coating of the stent does not fracture, peel off from the surface of the stent or become deformed when the stent is expanded during use, where stent expansion up to the required diameter at the site of the lesion can mean deforming it up to 300%.

Finding a polymer that fulfills all these requirements is currently one of the most important challenges in the field of DES, and it can be stated that the ideal coating for this kind of application has still not been developed.

WO 01/17578 describes a series of polymeric derivatives carrying triflusal or HTB based on homo- or copolymerization of an acrylic-type monomer carrying triflusal or HTB. As examples of polymers, the preparation of a homopolymer resulting from polymerization of 2-(methacryloyloxy)ethyl 2-acetyloxy-4-(trifluoromethyl)benzoate (THEMA) is described, as well as THEMA copolymers with N,N-dimethylacrylamide (DMA) or 2-acrylamido-2-methylpropanesulphonic acid (AMPS). The polymers described in this patent are indicated as useful for the coating of non-biological materials that will come into contact with blood during their use such as vascular prostheses, artificial cardiac valves, and stents due to their good properties from the standpoint of thrombogenicity.

Although the examples of polymers described in WO 01/17578 are stable, biocompatible, and show good anti-thrombogenic properties, they are not suitable for use as coating in DES since they do not have good adhesion to the stent surface nor sufficient flexibility to withstand the mechanical deformation that occurs during the manufacture and use of a stent.

There remains the need, thus, to find new polymers suitable for use as stent coating, and in particular having appropriate physico-mechanical properties including good adhesion to the stent and the capability of being stretched without flaking or cracking.

DESCRIPTION OF THE INVENTION

After thorough research to find a suitable polymer for use in DES, the present inventors have surprisingly found that certain copolymers based on THEMA and butyl acrylate in a specific range of molar fractions, as described below, exhibit very good physico-mechanical properties, including good adhesion to the stent and no crack-bridging, making them particularly suitable for use in the field of DES.

Thus, one aspect of the invention relates to a polymeric compound of formula I

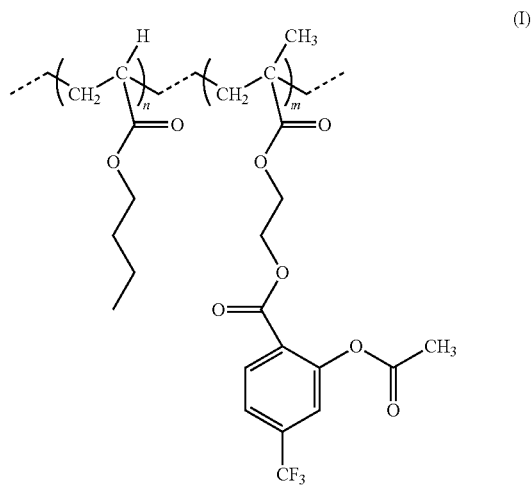

wherein:
m and n represent the molar fractions of the monomers in the polymer such that m+n is always 1 and where m represents a value between approximately 0.40 and approximately 0.52 and n represents a value between approximately 0.60 and approximately 0.48;
and where the monomer units are distributed randomly in the polymer.

In the formula I depicted above, the dashed line indicates polymer chains.

The polymers of formula I are capable of forming smooth, uniform coatings when applied on stents and exhibit excellent properties from the standpoint of adhesion, flexibility and crack-bridging, as explained in more detail in example 2. In addition, they show elevated stability under physiological conditions as well as good biocompatibility and are a good medium for the controlled release of drugs. All these properties make the polymers of the invention optimal candidates for the coating of stents, particularly for use in the field of DES.

In one embodiment of the invention, in a polymer of formula I m represents a value between 0.40 and 0.52 and n represents a value between 0.60 and 0.48 such that m+n is 1.

In another embodiment, m represents a value between approximately 0.42 and approximately 0.46 and n represents a value between approximately 0.58 and approximately 0.54 such that m+n is 1.

In another embodiment, m represents a value between 0.42 and 0.46 and n represents a value between 0.58 and 0.54 such that m+n is 1.

The polymeric compounds of formula I can be prepared by means of any of the known methods of radical polymerization. For example, they can be prepared by solution polymerization of THEMA and butyl acrylate, using feed rates of 65%-75% by weight of THEMA and 35%-25% by weight of butyl acrylate, in a suitable solvent and in the presence of a polymerization initiator. Said polymerization must be carried out in the absence of oxygen.

As initiator, any compound described in the literature for such purpose can be used, for example benzoyl peroxide, lauroyl peroxide, cumyl peroxide, butyl perbenzoate, 2,2'-azobisisobutyronitrile (AIBN) or 2,2'-azobisisopentanoic acid, among which benzoyl peroxide and 2,2'-azobisisobutyronitrile are preferred. The amount of initiator to be used will depend on the desired molecular weight, and will be easily determined by one skilled in the art.

Examples of suitable solvents for carrying out the polymerization include dioxane, dimethylformamide, isopropanol, mixtures of dioxane/water, chloroform, dimethyl sulphoxide, acetone, mixtures of acetone/dioxane and mixtures of acetone/water, among which the use of polar solvents such as dimethylformamide or solvating solvents such as dioxane or dioxane/water mixtures rich in dioxane are preferred.

The reaction temperature will depend on the initiator used and will also be a determining factor in the molecular weight of the resulting polymeric system, as will be known by those skilled in the art. When AIBN is used as an initiator, a temperature in the range of 50 to 70° C., preferably around 60° C., is appropriate.

With regard to the time of polymerization required, in general we have found that polymerization times of 24 to 64 hours are appropriate.

This process for the preparation of a polymer of formula I is another aspect of the present invention.

In a preferred embodiment, the polymeric compounds of formula I are prepared by radical polymerization in solution of THEMA and butyl acrylate in dioxane, in the absence of oxygen, using feed rates of 65%-75% by weight of THEMA and 35%-25% by weight of butyl acrylate, with a total monomer concentration in the solution in the range of 0.90-1 M, in the presence of 2,2-azobisisobutyronitrile (AIBN) with a concentration in the solution of about $1.5 \times 10^{-2}$ M, at a reaction temperature of about 60° C. and for a reaction time between 24 and 64 hours. In a more preferred embodiment, feed rates are 69%-71% by weight of THEMA and 31%-29% by weight of butyl acrylate.

Another aspect of the invention is a polymeric compound obtainable by the process described above.

The polymers of formula I are isolated using conventional methods, for example by precipitation in a suitable solvent such as ethanol, methanol, isopropanol, hexane, heptane, or diethyl ether, preferably ethanol. In general, it is advisable to use a high precipitant/solution ratio, that is of at least 10 times the volume of precipitant with regard to the volume of solution, to guarantee a good precipitation.

If desired, the polymers can be purified by conventional methods.

The starting monomer 2-(methacryloyloxy)ethyl 2-acetyloxy-4-(trifluoromethyl)benzoate (THEMA) can be prepared by following the process described in WO 01/17578. Butyl acrylate is commercially available. Both monomers can be purified by conventional processes.

As stated above, the polymeric compounds of the present invention are useful for coating the surface of stents. There are currently a variety of commercial stents of different types. Stents can be made of metal or polymeric materials. The material most commonly used in their manufacture is stainless steel, although other materials such as nitinol, tantalum or platinum, among others, are also used. Stents can have different structure designs as well as a variety of lengths or diameters, and can be self-expanding or expandable by means of a balloon. The polymers of the invention are useful for coating any type of stent.

Although they are specially designed for use in the field of stents, the polymers of the invention may also be used to coat other types of prostheses or medical devices made from materials of non-biological origin (whether metals, polymers, or any other synthetic material, to which we will commonly refer as non-biological materials) such as vascular prostheses or artificial cardiac valves.

Therefore, another aspect of the present invention is the use of a polymeric compound of formula I as a coating for non-biological materials, and particularly as a coating for stents. In a preferred embodiment, the stent is a metal stent.

Another aspect of the present invention is a medical device or article comprising a surface of a non-biological material coated with a polymer of formula I.

Another aspect of the present invention is a medical device or article comprising a surface of a non-biological material having a coating comprising a polymer of formula I.

In a preferred embodiment, the invention provides a stent having a coating comprising a polymer of formula I.

In a more preferred embodiment, the invention provides a stent having a coating comprising a polymer of formula I and one or more drugs physically incorporated or embedded in the polymer of formula I. Any type of drug or combination of drugs described in the literature that is useful in the field of restenosis (i.e. to reduce, inhibit or prevent restenosis) can be added, such as for example antiproliferative drugs, antineoplastic drugs, drugs interfering with the cell cycle or anti-inflammatory drugs. In a more preferred embodiment, the drug is selected from mTOR inhibitors such as rapamycin, everolimus or zotarolimus; calcineurin inhibitors such as tacrolimus, pimecrolimus or cyclosporin A; statins such as simvastatin, atorvastatin, pravastatin, fluvastatin or rosuvastatin; antimetabolites such as mycophenolic acid, azathioprine, 6-mercaptopurine, leflunomide or methotrexate; microtubule-interfering agents such as vinca alkaloids (e.g. vincristine or vinblastine) or taxanes (e.g. paclitaxel or docetaxel); RNA synthesis inhibitors such as actinomycin D; metalloproteinase inhibitors such as batimastat; corticosteroids such as dexamethasone, betamethasone or methylprednisolone; PDGF receptor inhibitors such as imatinib, AG-1295, or CGP-53716; and somatostatin receptor agonists such as angiopeptin; or any combination thereof. In a still more preferred embodiment, the drug is selected from rapamycin, everolimus, zotarolimus, tacrolimus, pimecrolimus, cyclosporin A, simvastatin, atorvastatin, pravastatin, fluvastatin, rosuvastatin, mycophenolic acid, azathioprine, 6-mercaptopurine, leflunomide, methotrexate, vincristine, vinblastine, paclitaxel, docetaxel, actinomycin D, batimastat, dexamethasone, betamethasone, methylprednisolone, imatinib, AG-1295, CGP-53716 and angiopeptin, or any combination thereof. The use of any of the above drugs in the form of a pharmaceutically acceptable salt thereof is encompassed within the scope of the invention.

The coatings with polymers of the invention can be applied by means of various known techniques such as by dipping in a solution of the polymer or by spraying a solution of the polymer on the stent or prosthesis to be coated, as well as by any other technique known by those skilled in the art. When the coating is also going to include a drug incorporated therein, the coating is prepared from a solution of the polymer and the drug in a suitable organic solvent, i.e. a solvent that is mutually compatible with the polymer and the drug and is capable of placing the polymer and drug into solution at the desired concentrations. As examples of suitable solvents, dioxane, tetrahydrofuran, and dimethylsulphoxide as well as mixtures thereof can be mentioned.

Figure 1:
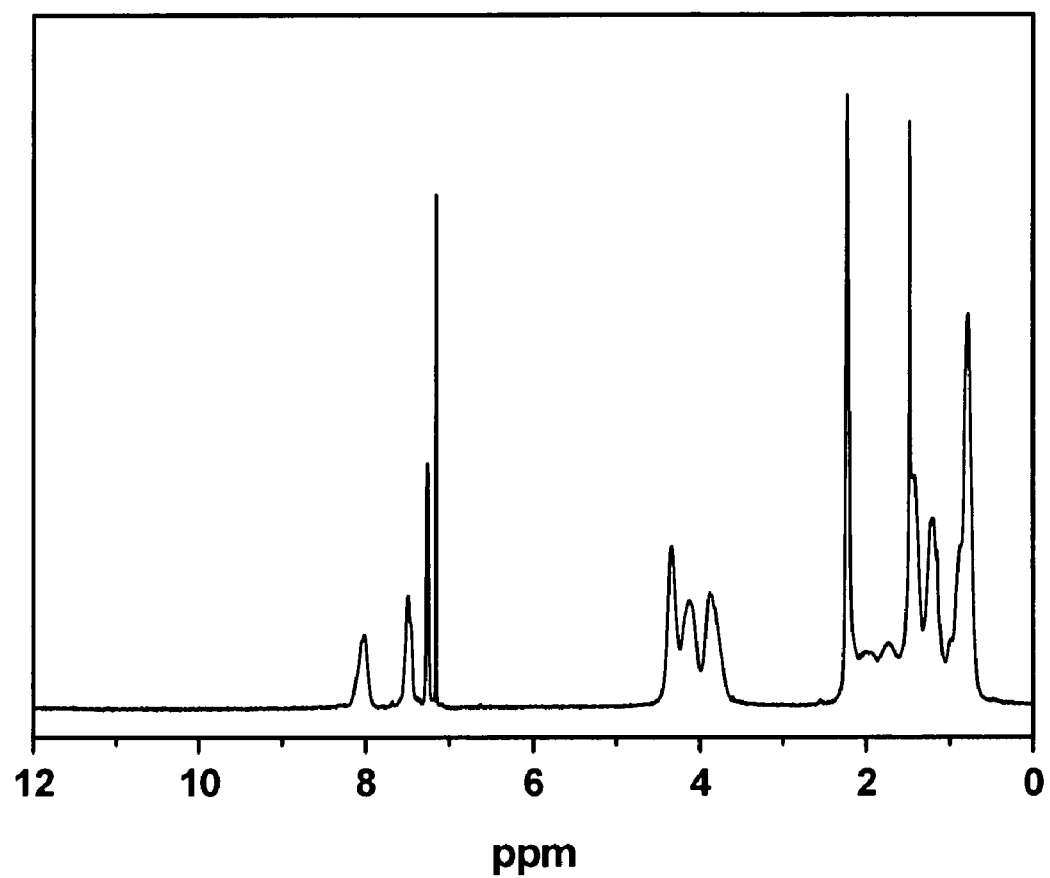
FIG. 1 shows the $^1$H-NMR spectrum of the polymer obtained in example 1.

The following examples are included herein to illustrate the preparation and uses of the compounds of the present invention and should not be interpreted as limiting the scope of the invention in any way.

EXAMPLES

The $^1$H-NMR spectrum (FIG. 1) was recorded in a Varian Gemini 200 unit using a 5% (w/v) solution in deuterated chloroform ($CDCl_3$).

The $^{13}$C-NMR spectrum (FIG. 2) was recorded in a Varian 300 unit using a 25% (w/v) solution in deuterated chloroform ($CDCl_3$).

The Fourier-transform infrared spectrum (FT-IR, FIG. 3) was recorded in a Perkin Elmer Spectrum One spectrometer, with a resolution of 4 $cm^{-1}$ and recording 4 scans. In this case, 5-mg samples of powdered polymer were used, using an attenuated total reflection (ATR) device.

The molar fractions m and n in the copolymer are determined by $^1$H-NMR analysis. Due to the experimental error of the method, deviations of up to 5% can exist in the value of these molar fractions.

The determination of the glass transition temperature ($T_g$) was carried out by differential scanning calorimetry (DSC) in a Perkin Elmer DSC 7 apparatus. In this case, a 15-mg sample of polymer was introduced in an aluminum cap, and after it was sealed by pressure, the $T_g$ was analyzed with a nitrogen stream of 50 mL/min at a constant heating speed of 10° C./min. The calibration of the apparatus temperatures was done using indium and zinc as standards. The glass transition was measured using the curve obtained in the second heating, taking as $T_g$ the temperature of the midpoint of the interval limited by the tangents before and after the changes in heat capacity with temperature (½ Δ Cp).

Example 1

Synthesis of a Copolymer of THEMA and Butyl Acrylate (BA) According to Formula I Corresponding to a Composition by Weight in the Feed of 70/30 THEMA/BA Preparation The synthesis of this copolymer was carried out by radical polymerization in purified dioxane using the THEMA monomer (obtained as described in WO 01/17578) and butyl acrylate (BA) in its commercial form (Aldrich), using 2,2-azobisisobutyronitrile (AIBN) as an initiator.

The dioxane (Panreac) was purified by distillation under a nitrogen stream over potassium hydroxide.

The 2,2-azobisisobutyronitrile (AIBN) (Fluka) was purified by recrystallization in methanol, melting point= 104±1° C.

The remaining reagents and solvents were used in their commercial form.

Experimental Process:

In a pyrex flask, 0.7 g of THEMA and 0.3 g of BA are dissolved in 4.53 mL of dioxane, wherein therefore the total concentration of monomers in the solution is 0.95 M. 11.14 mg of AIBN used as an initiator ($1.5 \times 10^{-2}$ M) are then added. Once this solution is prepared, a nitrogen stream is passed for thirty minutes. The closed flask is placed in an oven at 60° C. for 64 h. Following this time, the polymer is isolated by precipitation in an excess of ethanol and in an ice bath. To precipitate approx. 1 g of polymer, 800 mL of ethanol are used, over which the polymer solution is added dropwise. Once precipitated, the polymer is kept under stirring for 3 hours and is filtered, then washed with 500 mL of clean ethanol. It is then filtered and dried under vacuum to a constant weight. The reaction yield is around 80%.

Characterization

Figure 2:
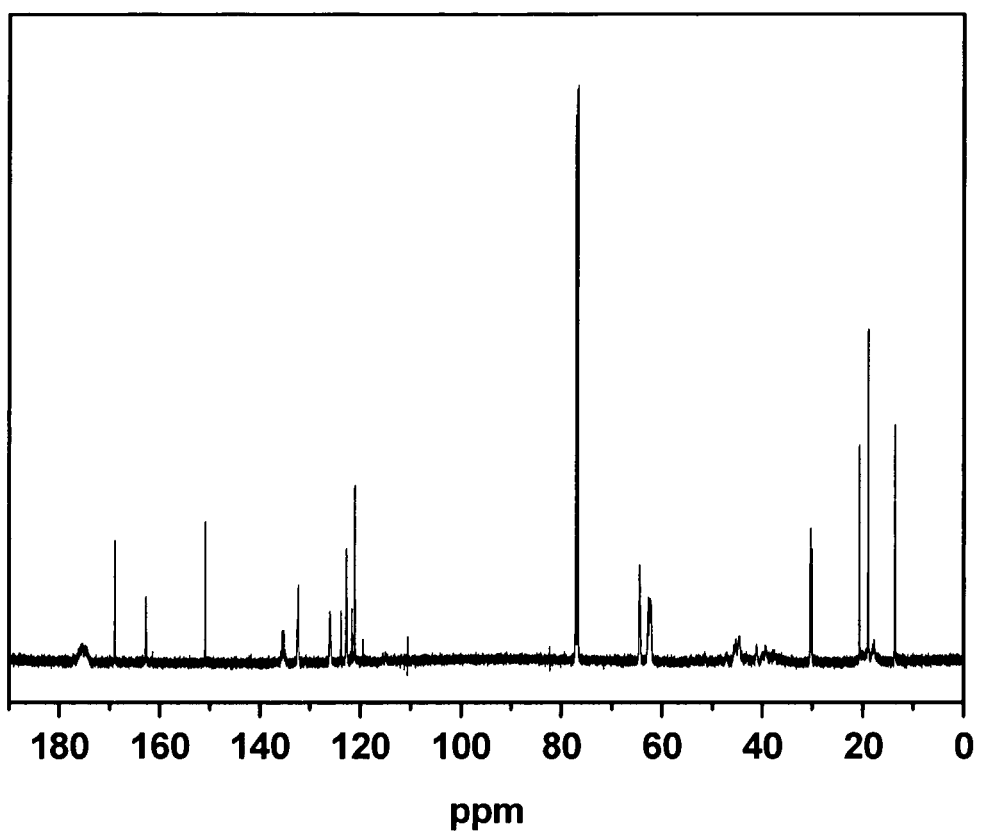
FIG. 2 shows the $^{13}$C-NMR spectrum of the polymer obtained in example 1.
Figure 3:
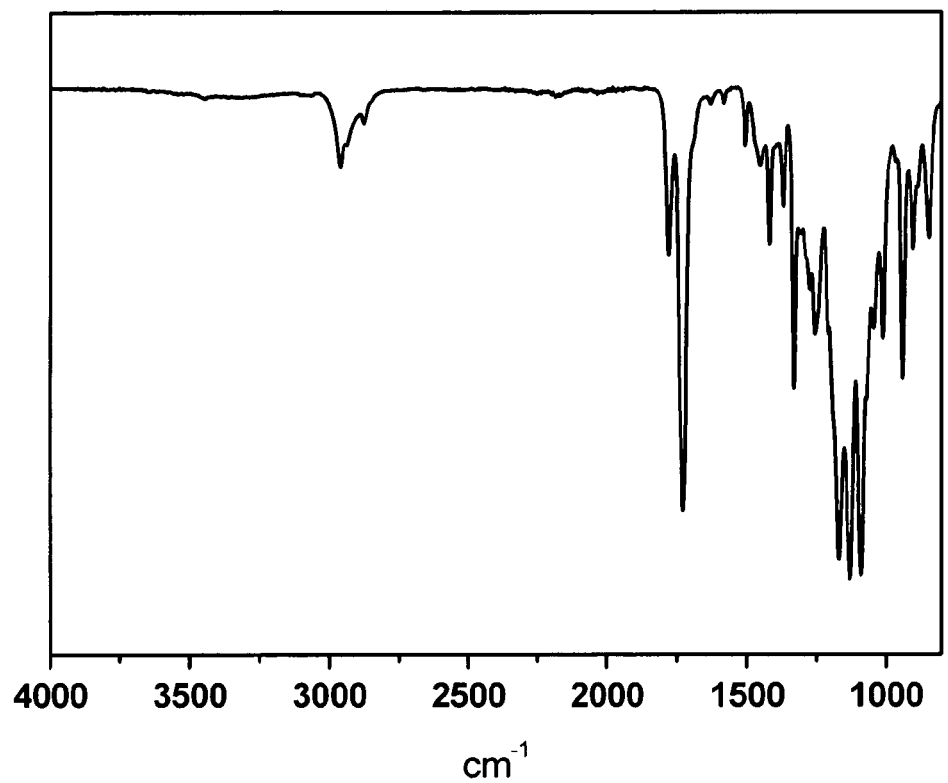
FIG. 3 shows the FTIR spectrum of the polymer obtained in example 1.

The $^1$H-NMR, $^{13}$C-NMR and FT-IR spectra of this polymer are shown in FIGS. 1 to 3, respectively.

Using the $^1$H-NMR spectrum, the molar fractions of both monomers in the polymer were calculated, obtaining values of m=0.44±0.02 (THEMA) and n=0.56±0.02 (BA).

The $T_g$ value obtained for the polymer of this example was 21±2° C. (average value of three samples analyzed separately).

Example 2

Preparation of a Coating with a Polymer of Formula I and Determination of the Crack-Bridging and Adhesion to a Metal Stent A solution of the polymer obtained in example 1 is prepared using dioxane as a solvent and a concentration of 4% by weight. The polymer solution prepared is applied to a metal stent with a length of 14 mm, by means of spraying, until an overall coating of approximately 300 micrograms is obtained.

The resulting coated stent is mounted on a deployment balloon with a length of 15 mm and diameter of 3.5 mm, is packaged, and sterilized with ethylene oxide.

Once sterilized, the balloon is inflated at a pressure of 8 atmospheres to achieve the nominal diameter of 3.5 mm. The balloon is then deflated and the expanded stent is withdrawn.

The expanded coated stent is then observed with the aid of an optical microscope. The adhesion and crack-bridging behavior of the polymer of example 1 was proven to be excellent, since the coating remained adhered to the stent and showed no points of flaking, cracking or delamination.

Same good results were obtained with stents coated following the procedure described above using a solution of polymer of example 1 and simvastatin in dioxane.

The same experiment carried out with stents coated with the copolymers poly(THEMA-co-DMA) described in WO 01/17578 shows poor adhesion of the polymer to the stent and crack-bridging behavior, resulting in many areas of flaking and cracking of the polymer coating, which renders said polymers unsuitable for use in coating of stents.

The invention claimed is:

1. A polymeric compound of formula I

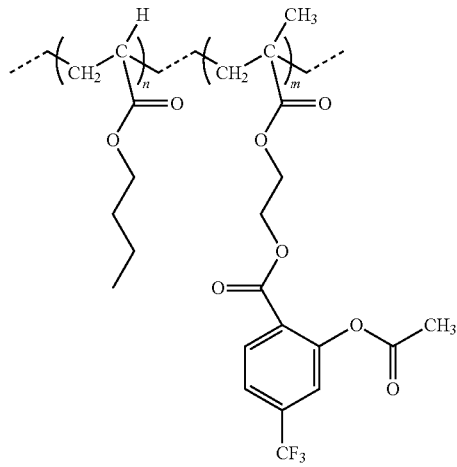

(I)

wherein:
m and n represent the molar fractions of the monomers in the polymer such that m+n is always 1 and where m represents a value between approximately 0.40 and approximately 0.52 and n represents a value between approximately 0.60 and approximately 0.48; and wherein the monomer units are distributed randomly in the polymer.

2. A compound according to claim 1 wherein m represents a value between 0.40 and 0.52 and n represents a value between 0.60 and 0.48 such that m+n is 1.

3. A compound according to claim 1 wherein m represents a value between approximately 0.42 and approximately 0.46 and n represents a value between approximately 0.58 and approximately 0.54 such that m+n is 1.

4. A compound according to claim 1 wherein m represents a value between 0.42 and 0.46 and n represents a value between 0.58 and 0.54 such that m+n is 1.

5. A process for the preparation of a polymeric compound of formula I according to claim 1 which comprises the polymerization in solution of 2-(methacryloyloxy)ethyl 2-acetyloxy-4-(trifluoromethyl)benzoate (THEMA) and butyl acrylate, using feed rates of 65%-75% by weight of THEMA and 35%-25% by weight of butyl acrylate, in a suitable solvent and in the presence of a polymerization initiator, in the absence of oxygen.

6. A process according to claim 5 wherein the solvent is dioxane, the initiator is 2,2-azobisisobutyronitrile (AIBN), and the reaction is carried out at a temperature between 50 and 70° C. and for a reaction time of 24 to 64 h.

7. A process according to claim 6 wherein the total concentration of the monomers in the solution is in the range of 0.90-1 M, the concentration of AIBN in the solution is about $1.5 \times 10^{-2}$ M, and the reaction temperature is about 60° C.

8. A process according to claim 7 wherein feed rates are 69%-71% by weight of THEMA and 31%-29% by weight of butyl acrylate.

9. A polymeric compound of formula I according to claim 1 prepared by a process which comprises the polymerization in solution of 2-(methacryloyloxy)ethyl 2-acetyloxy-4-(trifluoromethyl)benzoate (THEMA) and butyl acrylate, using feed rates of 65%-75% by weight of THEMA and 35%-25% by of butyl acrylate, in a suitable solvent and in the presence of a polymerization initiator, in the absence of oxygen.

10. A medical device or article comprising a surface of a non-biological material having a coating comprising a polymer of formula I according to claim 1 or 9.

11. A medical device according to claim 10 wherein the device is a stent.

12. A medical device according to claim 11 wherein the stent coating additionally comprises one or more drugs physically incorporated or embedded in the polymer of formula I.

13. A stent according to claim 12 wherein the drug is rapamycin, everolimus, zotarolimus, tacrolimus, pimecrolimus, cyclosporin A, simvastatin, atorvastatin, pravastatin, fluvastatin, rosuvastatin, mycophenolic acid, azathioprine, 6-mercaptopurine, leflunomide, methotrexate, vincristine, vinblastine, paclitaxel, docetaxel, actinomycin D, batimastat, dexamethasone, betamethasone, methylprednisolone, imatinib, AG-1295, CGP-53716, angiopeptin, or any combination thereof.

* * * * *

UNITED STATES PATENT AND TRADEMARK OFFICE
CERTIFICATE OF CORRECTION

PATENT NO. : 8,309,105 B2
APPLICATION NO. : 12/067563
DATED : November 13, 2012
INVENTOR(S) : San Roman Del Barrio et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,121 days.

Signed and Sealed this
Second Day of April, 2013

Teresa Stanek Rea
*Acting Director of the United States Patent and Trademark Office*